United States Patent [19]

Hiramoto et al.

[11] Patent Number: 6,110,355
[45] Date of Patent: Aug. 29, 2000

[54] CORROSION TESTING METHOD

[75] Inventors: Osamu Hiramoto; Atsuko Nomiyama, both of Kanagawa; Shoko Akimoto, Tokyo, all of Japan

[73] Assignee: Sony Corporation, Tokyo, Japan

[21] Appl. No.: 09/217,908

[22] Filed: Dec. 22, 1998

[30] Foreign Application Priority Data

Dec. 26, 1997 [JP] Japan ................................ 9-366979

[51] Int. Cl.⁷ .................................................. G01N 17/02
[52] U.S. Cl. ........................ 205/775.5; 205/763; 205/767; 422/7
[58] Field of Search ................................ 205/775.5, 763, 205/767; 422/7

[56] References Cited

U.S. PATENT DOCUMENTS 4,060,461  11/1977  Seyl ...................................... 205/755.5

*Primary Examiner*—Bruce F. Bell
*Attorney, Agent, or Firm*—Hill & Simpson

[57] ABSTRACT

A corrosion testing method in which testing conditions can be set easily and the corrosion advancing degree of the silver or silver alloys over a longer time period can be evaluated in a shorter time duration. In the present corrosion testing method, in evaluating the state of corrosion of the silver or silver alloys in a natural environment, an acceleration test is carried out by exposing a silver piece to an atmosphere of a gas mixture obtained on mixing only hydrogen sulfide and nitrogen dioxide in clean air.

10 Claims, 7 Drawing Sheets

CORROSION TESTING METHOD

BACKGROUND OF THE INVENTION

1. Field of the Invention

This invention relates to a corrosion testing method used in evaluating the corroded state of silver or silver alloys used in an electronic equipment for accelerated reproduction of the corrosion of the silver or silver alloys.

2. Description of the Related Art

Up to now, contact parts, such as switches or potentiometers, are routinely formed of silver or silver alloys as a contact material. These materials are hereinafter referred to as a silver-based contact part. On prolonged use by customers, these silver-based contact parts tend to undergo the corrosion of silver to give rise to contact troubles.

It is therefore necessary to evaluate long-term reliability of the silver-based contact parts and hence a variety of corrosion testing methods are presently used. Recently, in these corrosion tests, a gas mixture composed of plural gases is preferentially used for improving the reproducibility.

A number of testing methods have been reported by business concerns and research organizations, and a number of researches have been conducted. Specifically, these corrosion tests are conducted by setting up the atmosphere in which a silver-based contact part, if allowed to stand therein, is to undergo the state of corrosion, and by actually allowing the silver-based contact parts to stand therein.

With these testing methods, it is extremely difficult to set up a condition conforming to the targeted environment because the gas mixture is usually composed of three or more gas components. Moreover, although it is confirmed by these testing methods that the metals such as silver tends to undergo the corrosion, sufficient investigations into the correlation between the corrosion speed in the test environment and that in the actual operating environment have not been conducted to date.

Thus, in the conventional testing method, it has not been possible to reproduce and individually evaluate the advancing degree of the corrosion in the actual operating environment, even though relative corrosion evaluation can be achieved on plural different samples.

Therefore, in the conventional testing method, it has been necessary to approximate the testing condition to the actual using condition for evaluating the corrosion advancing degree in the actual using environment. Specifically, the conventional testing methods were conducted under a low concentration of the gas mixture as low as the ppb order, which accounts for the difficulty met in setting the aforementioned testing conditions.

Moreover, in the conventional testing methods, in which the gas mixture concentration is set to a lower value, the protracted testing time as long as two to three months is required for evaluating the long-term durability. This accounted for poor efficiency of the conventional testing method and difficulty met in achieving accurate evaluation.

Among the above-mentioned corrosion testing methods, a testing method prescribed in the standard for International Electrotechnical Commission (IEC) is in widespread use as a testing method for reproducing the corrosion of the metallic materials used as the contact materials for the electrical equipments. However, this IEC standard similarly suffers from the above-mentioned various drawbacks because the gas mixture is usually employed at a concentration of the order of ppbs.

SUMMARY OF THE INVENTION

It is therefore an object of the present invention to eliminate the above drawbacks and to provide a corrosion testing method whereby the testing conditions can be set with relative ease and whereby the long-term corrosion advancing degree in silver or silver alloys can be evaluated in a short time.

For accomplishing the above object, the present inventors have conducted perseverant researches, and have clarified the corrosion mechanism and the corrosion speed in silver or silver alloy. Based on this corrosion speed, the present inventors have succeeded in carrying out an accelerated test, using an accurately calculated acceleration constant, and thus arrived at the present invention.

According to the present invention, there is provided a corrosion testing method wherein, in evaluating the state of corrosion of the silver or silver alloys in a natural environment, an acceleration test is carried out by exposing a silver piece to an atmosphere of a gas mixture obtained on mixing only hydrogen sulfide and nitrogen dioxide in clean air.

In the present corrosion testing method, the silver (Ag) or silver alloys is reacted with hydrogen sulfide ($H_2S$) to yield silver sulfide ($Ag_2S$). This silver sulfide is equivalent to that yielded in a natural environment, and is mainly responsible for corrosion of the silver or silver alloys. In the present technique, nitrogen dioxide ($NO_2$) acts as a catalyst for accelerating the reaction between silver or silver alloys and hydrogen sulfide. In the present technique, the testing method is conducted under this specified atmosphere to reproduce the natural environment faithfully to realize the acceleration test having high operational reliability.

With the corrosion testing method of the present invention, the state of corrosion in the natural environment can be reproduced by an acceleration test of exposing a silver piece to the atmosphere of a gas mixture obtained on mixing only hydrogen sulfide and nitrogen dioxide in clean air. Thus, with the present technique, the gas mixture can be produced easily, while the long-term corrosion under the natural environment can be reproduced in a short time. Therefore, this technique enables reliability evaluation for corrosion in a short time on silver or silver alloys.

DESCRIPTION OF THE PREFERRED EMBODIMENTS

Figure 1:
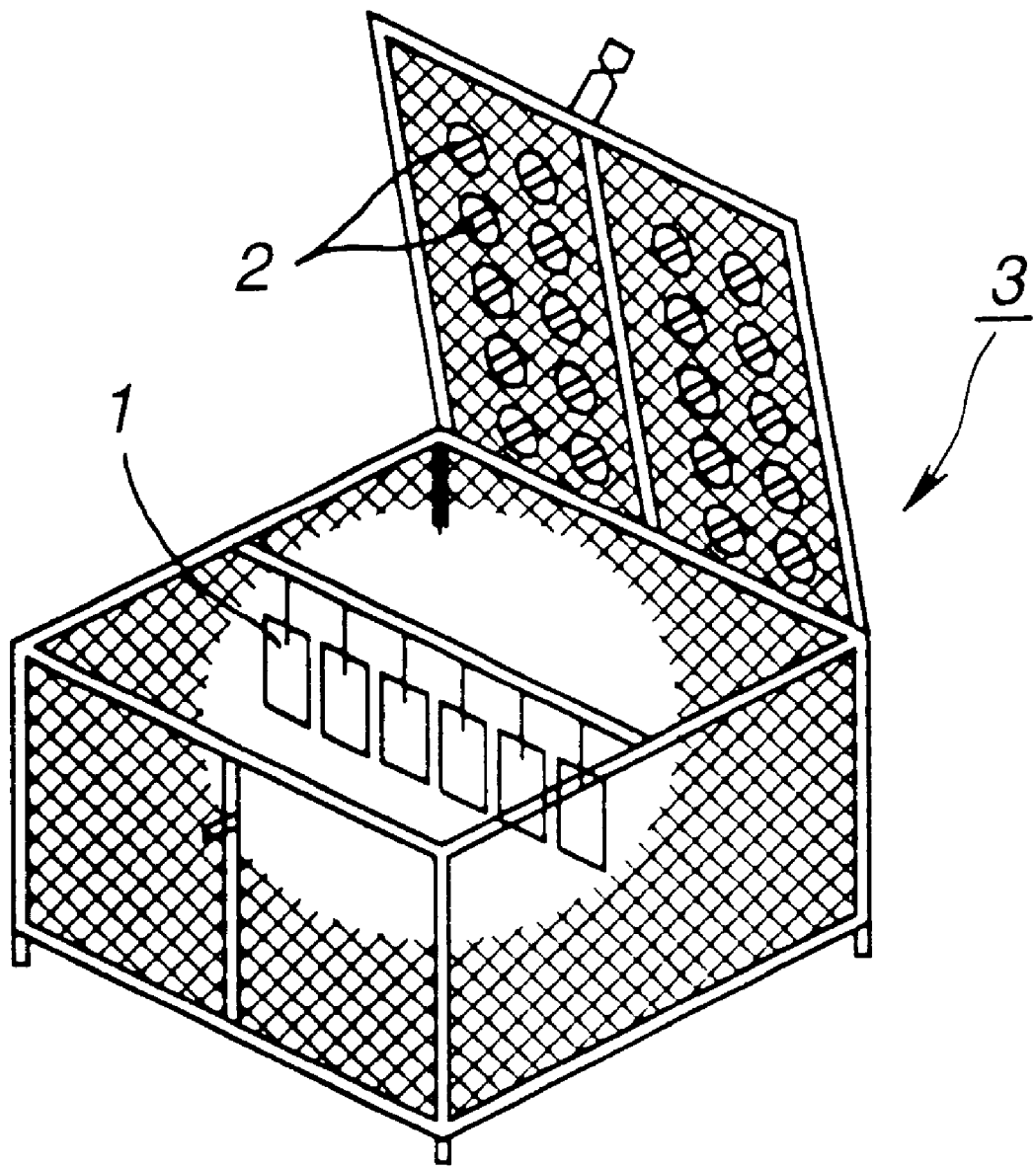
FIG. 1 is a schematic perspective view of a cage used for monitoring.

Referring to the drawings, the corrosion testing method according to a preferred embodiments of the present invention will be explained in detail.

The corrosion testing method according to the present invention finds the state of corrosion under the natural environment of the silver or silver alloys used in an electrical equipment by an accelerated test. Specifically, this technique reproduces the corrosion produced on prolonged use in the natural environment in a shorter time.

First, the corrosion produced on prolonged use of the silver or silver alloys under the natural environment is explained.

Under the natural environment, the silver or silver alloys is reacted with a trace amount of corrosive components contained in air. For comprehending this state of corrosion, the state of corrosion was monitored with South-eastern Asia, Europe and America and Japan as the monitoring sites. For monitoring the state of corrosion, an air-permeable basket 3, having a silver test piece 1 and a silver-based contact part 2 mounted therein, was allowed to stand as shown in FIG. 1.

This basket 3, formed of, for example, stainless steel, was installed indoors, such as in a sitting room of a common dwelling house, and outdoors, such as at an eave. Specifically, a number of these baskets were installed at twelve sites in each of six nations of South Eastern Asia, five nations in Europe and America and in Japan. As the silver test piece 1, a silver plate 50 mm long, 10 mm width and 1 mm thickness, was used. As the silver-based contact part 2, two different types of switches and a single type of a potentiometer were used.

This monitoring was carried out for one year and the silver test piece 1 and the silver-based contact part 2 were recovered at intervals of one, two, three, six, nine and twelve months. In the monitoring, the corrosion products of the recovered silver test pieces 1 were identified by estimation from the reduction potential of the coulometric reduction method and an energy dispersive X-ray spectroscopy. Also, of the recovered silver test pieces 1, the film thicknesses of the corrosion products as calculated by the electric quantity in coulombs by the coulmetric reduction method were measured, and surface properties of the corrosion products were observed under a scanning elecron microscope (SEM).

Figure 2:
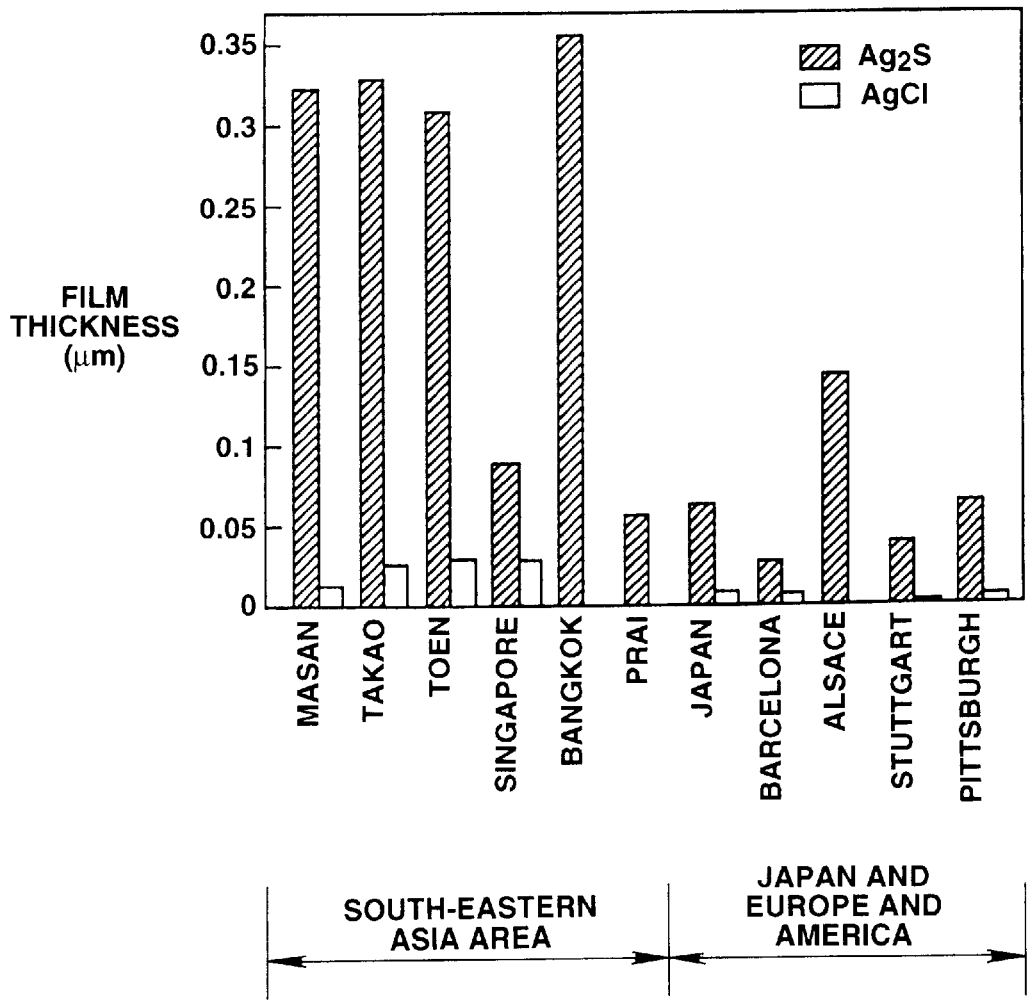
FIG. 2 is a bar graph showing the types of the corrosion products in monitoring nations and the film thickness.
Figure 3:
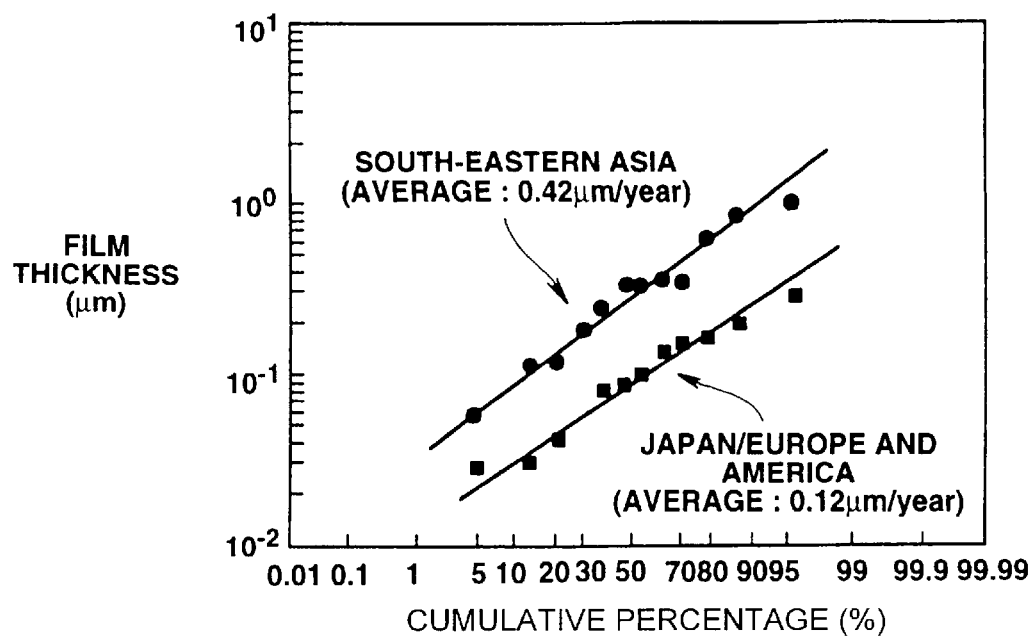
FIG. 3 is a graph showing the distribution of the film thickness of silver corrosion products under a natural environment.

FIG. 2 shows the identified results of the silver corrosion products under the natural environment. As may be seen from FIG. 2, silver corrosion products were silver sulfide ($Ag_2S$) and silver chloride (AgCl), both indoors and outdoors, irrespective of the monitoring nations. The silver corrosion products were predominantly silver sulfide. As may also be seen from FIGS. 2 and 3, corrosion is severer in South eastern Asia than in Europe and America and in Japan. In FIG. 3, the cumulative percentage and the film thickness are plotted in the logarithmic scale on the abscissa and in the normal seale on the ordinate, respectively.

Figure 4:
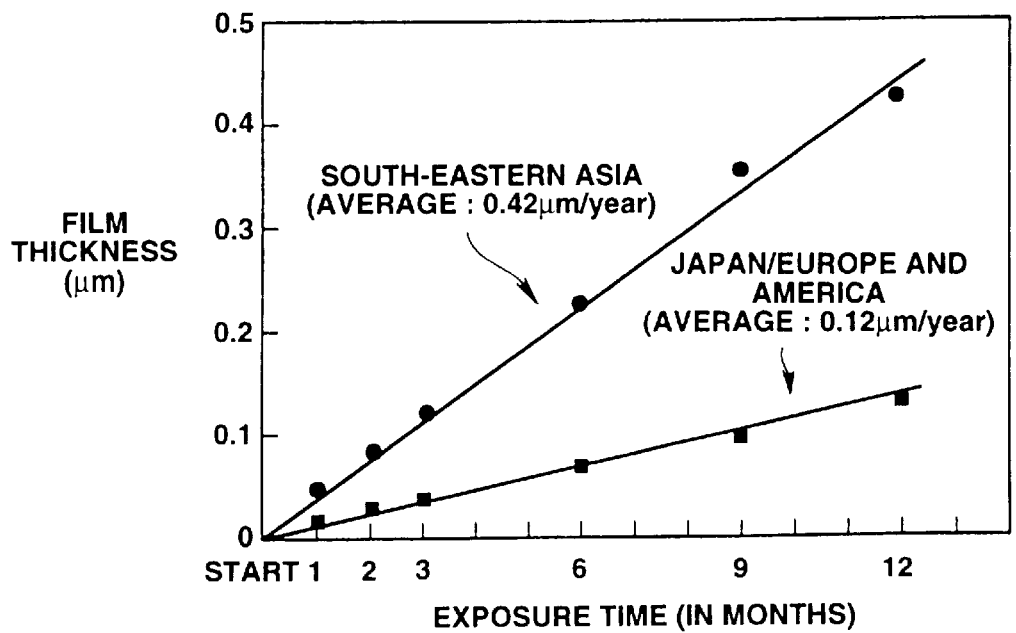
FIG. 4 is a graph showing the relation between the exposure time under the natural environment and the film thickness of the corrosion product.

The relation between the time the test pieces are allowed to stand in the natural environment, that is the exposure time, and the film thickness of the corrosion products, is shown in FIG. 4. As may be seen from FIG. 4, the film thickness of the corrosion products is increased linearly with the exposure time, in South Eastern Asia, in Europe and America, and in Japan. Specifically, the film thickness is increased at a rate approximately of 0.42 µm/year in South eastern Asia and at a rate of approximately 0.12 µm/year in Europe and America and in Japan.

Figure 5:
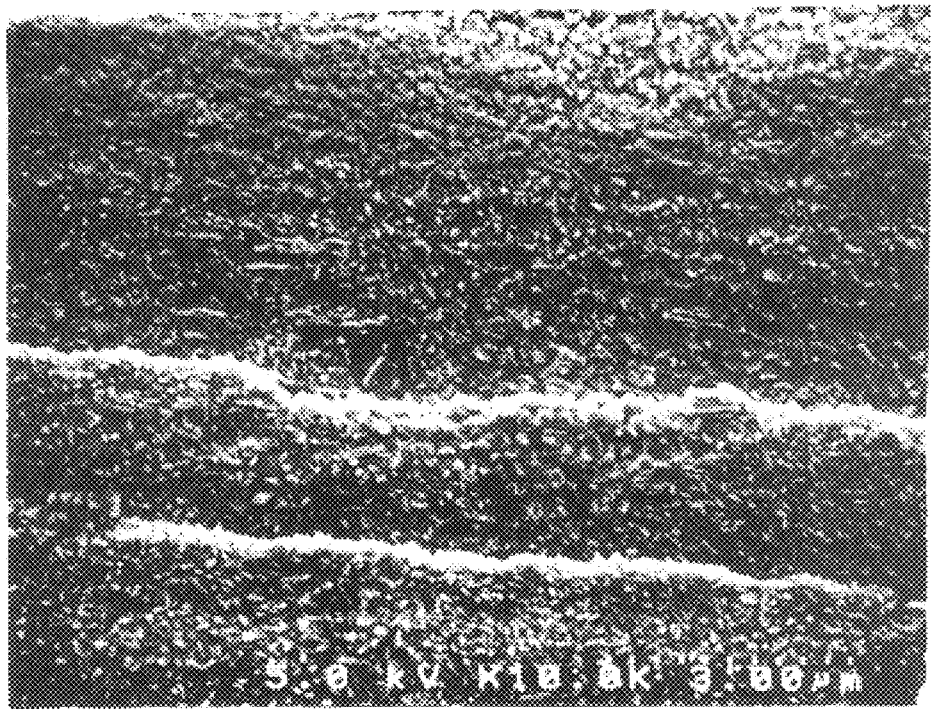
FIG. 5 is a SEM photo for illustrating the crystallized state of the corrosion products when allowed to stand for three months in South-Eastern Asia.
Figure 6:
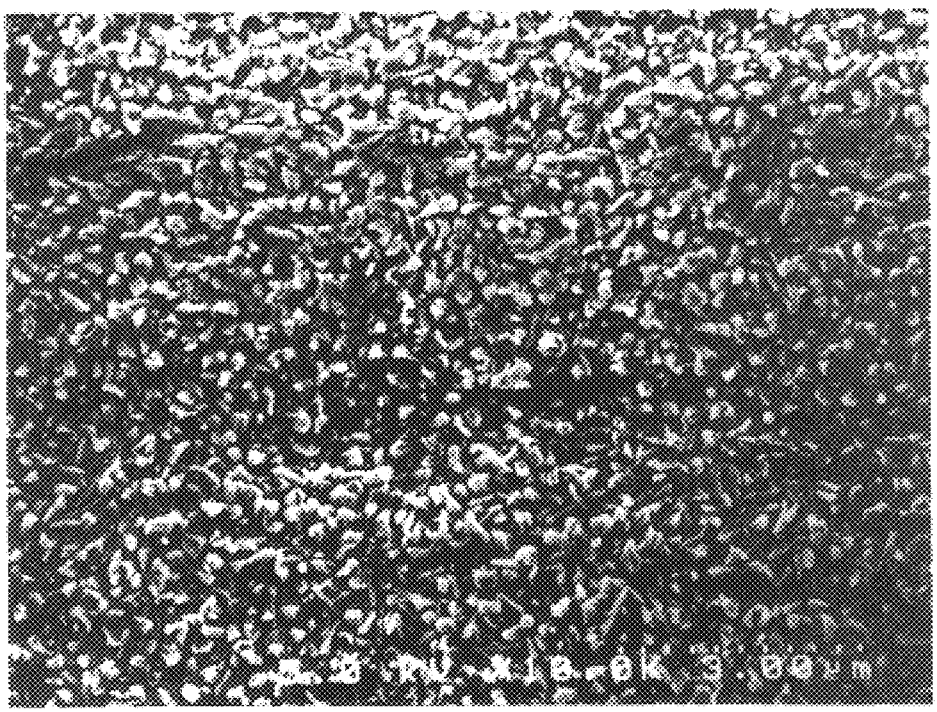
FIG. 6 is a SEM photo for illustrating the crystallized state of the corrosion products when allowed to stand for twelve months in South-Eastern Asia.
Figure 7:
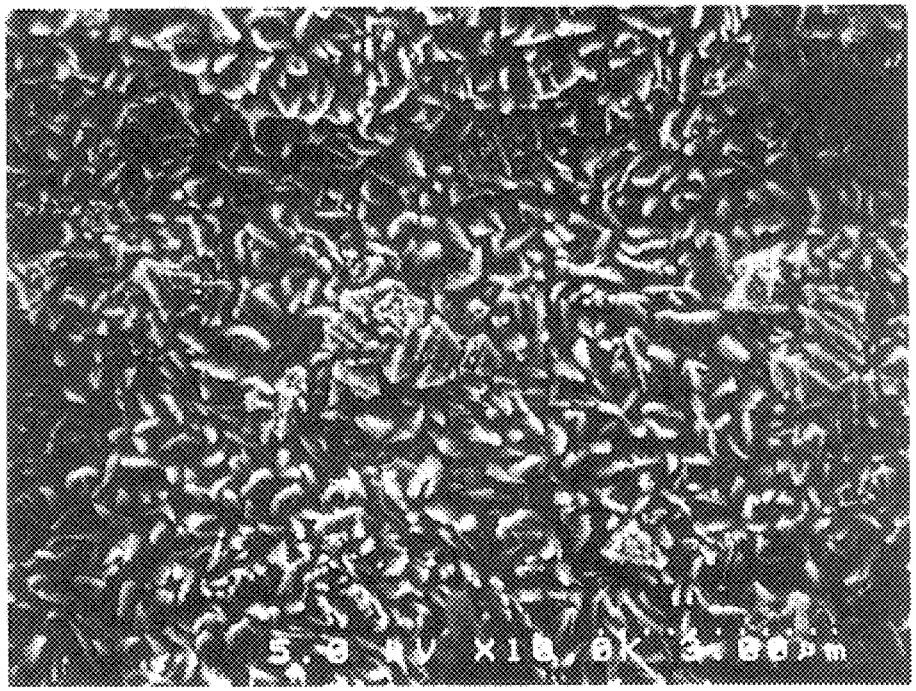
FIG. 7 is a SEM photo for illustrating the crystallized state of the corrosion product containing silver chloride.

The surface of the corrosion products, as photographed by SEM, was of the appearance shown in FIG. 5 to 7. These FIG. 5 to 7 are SEM photos taken with a magnification of 10,000. The corrosion products shown in FIG. 5 are those formed on allowing the test piece to stand for three months on test sites of the South Eastern Asia and are of a dense crystal structure of silver sulfide. The corrosion products shown in FIG. 6 are those formed on allowing the test piece to stand for twelve months on test sites of the South eastern Asia. These present a crystal structure coarser in grain size than that of the corrosion products shown in FIG. 5. On the other hand, the corrosion products shown in FIG. 7 are composed of both silver sulfide and silver chloride and are of the crystal structure of silver chloride of a coarser grain size and a dense silver sulfide film.

From the foregoing, it may be seen that silver or silver alloys undergo corrosion in natural environment at a corrosion speed of approximately 0.42 µm/year such that silver sulfide having a dense crystal structure has been formed on the surface region.

The corrosion testing method, consisting in reproducing the corrosion under the natural environment to evaluate the state of corrosion of the silver or silver alloys, is hereinafter explained.

In the present corrosion testing method, a gas mixture composed only of hydrogen sulfide ($H_2S$) and nitrogen dioxide ($NO_2$) was produced. A silver test piece and a silver-based contact part were exposed to an atmosphere obtained on mixing this gas mixture with clean air. With this technique, silver is reacted with hydrogen sulfide to form a layer of silver sulfide. This silver sulfide, which is yielded on exposure of the silver or silver alloys to the natural environment, mainly accounts for corrosion occurring in silver or silver alloys.

With this technique, nitrogen dioxide, contained in the gas mixture, serves as a reaction catalyst between hydrogen sulfide and silver. This facilitates the reaction between hydrogen sulfide and silver to form the corrosion products in a shorter time.

Since the gas mixture is composed only of hydrogen sulfide ($H_2S$) and nitrogen dioxide ($NO_2$), it can be generated easily. That is, since the gas mixture is free from other trace components, the gas mixture can be yielded easily.

The gas mixture preferably has a hydrogen sulfide to nitrogen dioxide concentration ratio of 1:1 to 1:3. If the gas mixture composition is in this range, the reaction between hydrogen sulfide and silver can proceed smoothly to carry out the desired accelerated test. However, if the mixing ratio of nitrogen dioxide to hydrogen sulfide is not larger than 1, the catalytic effect of nitrogen dioxide can hardly be displayed to retard the reaction rate between hydrogen sulfide and silver. If the mixing ratio of nitrogen dioxide to hydrogen sulfide exceed 3, there is the risk that the crystal structure of silver sulfide as a corrosion product is not the same as that of the actually produced corrosion product.

After exposing the silver contact part and the silver-based test piece to the gas mixture for a predetermined time, the film thickness of the silver sulfide layer is measured. By controlling the time of exposure of the test pieces (exposure time) and the concentration of the gas mixture, the corrosion advancing state over a prolonged time in natural environment can be reproduced in a shorter time.

In this gas mixture, it is preferred that hydrogen sulfide and nitrogen dioxide be of the concentration of 0.7 to 2.0 ppm and 1.5 to 4.0 ppm, respectively. If the concentrations of hydrogen sulfide and nitrogen dioxide are in these ranges, it is possible to carry out the corrosion test under optimum conditions of acceleration.

If the gas mixture is in this concentration range, silver sulfide corresponding to that formed over five to ten years under the natural environment can be produced on exposure for about four days. However, if the hydrogen sulfide concentration is 0.7 ppm or less, the conditions of acceleration are not optimum, such that exposure time slightly longer than the above time may be consumed until the desired film thickness is achieved.

In the present technique, an atmosphere corresponding to five to ten years under the natural environment can be produced by exposure continuing for about four days. That is, with the present technique, the silver-based contact parts formed of silver or silver alloys can be evaluated as to operational reliability under the natural environment over a shorter time duration.

EXAMPLES

The present invention will be explained with reference to Examples 1 to 12 for the corrosion testing methods according to the present invention.

Examples 1 to 12

In these Examples 1 to 12, the concentrations of hydrogen sulfide and nitrogen dioxide are set as shown in the following Table 1.

TABLE 1

| Examples | $H_2S$ concentration (ppm) | $NO_2$ concentration (ppm) | temperature (° C.)/humidity (% RH) | test duration time |
|---|---|---|---|---|
| Ex. 1 | 0.7 | 1.5 | 30° C./ | four days |
| Ex. 2 | 1.0 | 1.5 | 70% RH | |
| Ex. 3 | 1.0 | 2.0 | | |
| Ex. 4 | 1.0 | 3.0 | | |
| Ex. 5 | 1.0 | 4.0 | | |
| Ex. 6 | 1.5 | 1.5 | | |
| Ex. 7 | 1.5 | 2.0 | | |
| Ex. 8 | 1.5 | 3.0 | | |
| Ex. 9 | 1.5 | 4.0 | | |
| Ex. 10 | 2.0 | 2.0 | | |
| Ex. 11 | 2.0 | 3.0 | | |
| Ex. 12 | 2.0 | 4.0 | | |

As may be seen from Table 1, the hydrogen sulfide concentrations were set to 0.7 ppm. 1.0 ppm, 1.5 ppm and to 2.0 ppm for Example 1, Examples 2 to 5, Examples 6 to 9 and for Examples 10 to 12, respectively.

In the Examples 2 to 5, the nitrogen dioxide concentrations were set to 1.5 ppm, 2.0 ppm, 3.0 ppm and to 4.0 ppm, respectively, for adjusting the hydrogen sulfide to nitrogen dioxide concentration ratio. In the Examples 6 to 9, the nitrogen dioxide concentrations were set to 1.5 ppm, 2.0 ppm, 3.0 ppm and to 4.0 ppm, respectively, for adjusting the hydrogen sulfide to nitrogen dioxide concentration ratio, whereas, in the Examples 10 to 12, the nitrogen dioxide concentrations were set to 2.0 ppm, 3.0 ppm and to 4.0 ppm, respectively, for adjusting the hydrogen sulfide to nitrogen dioxide concentration ratio.

Figure 8:
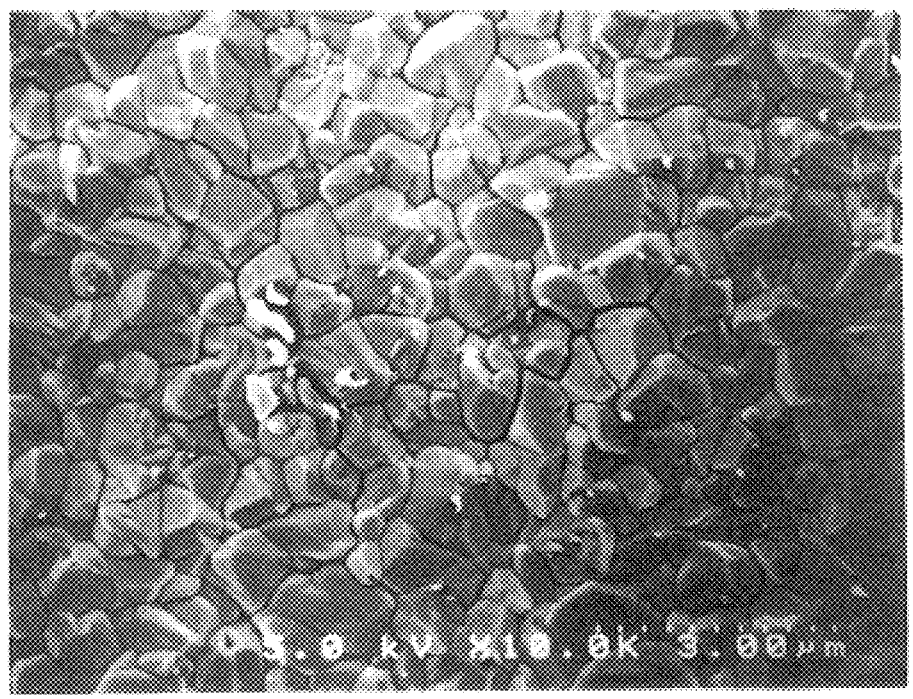
FIG. 8 is a SEM photo for illustrating the crystallized state of the corrosion product produced by the present technique.

In the above Examples, an atmosphere in which to allow the silver test piece to stand was selected so that the temperature and the humidity were 30° C. and 70%RH, respectively. Under these conditions, the silver test piece was allowed to stand for four days and the film thickness of the yielded silver sulfide was subsequently measured. Comparative Example For comparison to the Examples 1 to 12, the film thickness of the yielded silver sulfide was measured in the same manner as in Example 1 under the conditions specified under IEC. Specifically, this IEC standard provides that the concentrations of hydrogen sulfide, nitrogen dioxide and chlorine be 0.1±0.02 ppm, 0.2±0.05 ppm and 0.02±0.005 ppm, respectively. Moreover, in the present Comparative Example, the atmosphere in which to allow the silver test piece to stand was set to the temperature of 30±1° C. and 75±3%RH, respectively. Results FIG. 8 shows a SEM photo for observing the surface state of the silver test piece corroded by the technique shown in the Examples 1 to 12. On comparing the SEM photo shown in FIG. 8 to this SEM photo of the silver test piece corroded under the natural environment shown in FIG. 5 to 7, these photos may be said to be equivalent in that silver sulfide crystals are formed densely. Thus, it may be seen that the Examples 1 to2 reproduce the state of corrosion of the silver or silver alloys under the natural environment. Since the concentration ratio of hydrogen sulfide to nitrogen dioxide is higher than 1:3 in the Examples 4, 5 and 9, the state of corrosion is slightly different from the state of corrosion of the silver or silver alloys under the natural environment.

Figure 9:
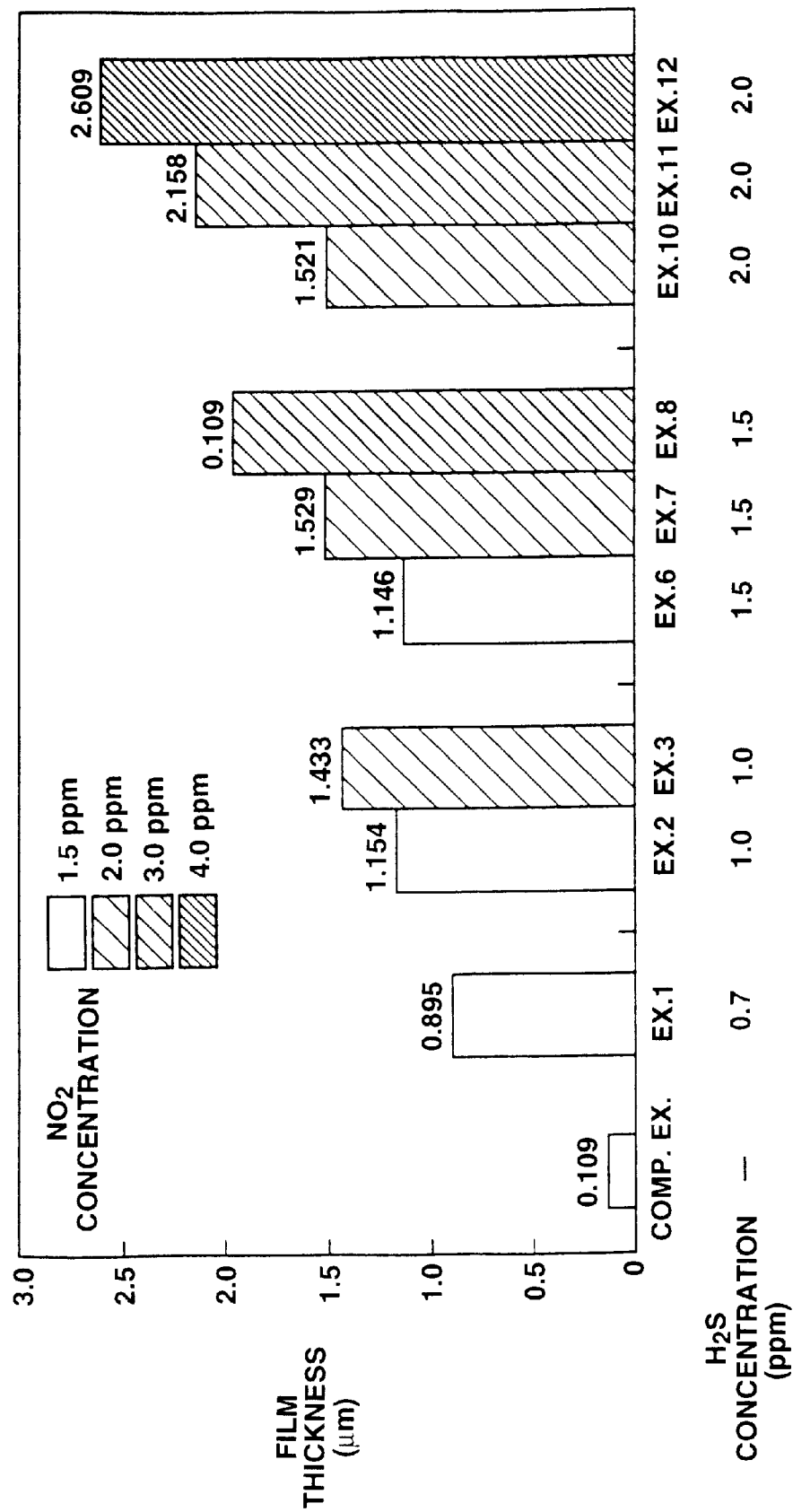
FIG. 9 is a bar graph showing the film thicknesses of corrosion products formed by the techniques of Examples 1 to 12 and the Comparative Example.
Figure 10:
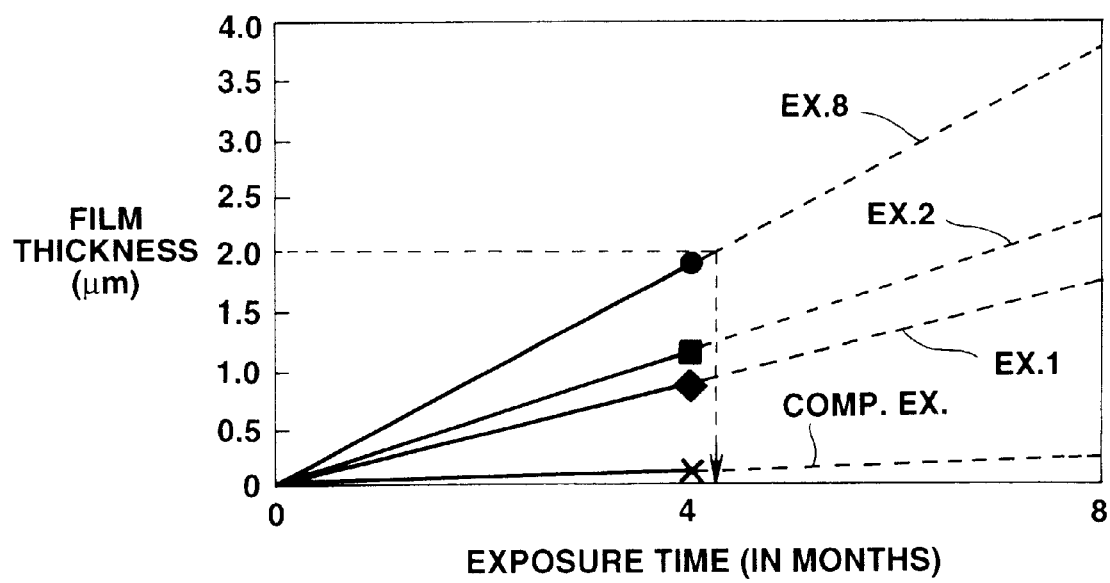
FIG. 10 is a graph for illustrating the relation between the exposure time in the Examples 1, 2 and 8 and the Comparative Example and the film thickness of the corrosion product.

The film thicknesses of silver sulfide of Examples 1 to 12 and the Comparative Example are shown in FIG. 9. Keeping in mind that the film thickness of silver sulfide increases with exposure time, if the relation between the exposure time and the film thickness of silver sulfide in the Examples 1, 2 and 8 and in the Comparative Example is shown in a graph, the result is as shown in FIG. 10. As may be seen from FIG. 9 and 10, only silver sulfide with a film thickness of the order of 0.1 μm was formed in the corrosion test conforming to the IEC standard given as the Comparative Example. Since silver sulfide is formed at a rate of 0.4 μm per year in South Eastern Asia, it took about 16 days to reproduce the corrosion advancing rate per year if the technique of the Comparative Example was followed. It was also seen that the time duration of about 80 days was required until the corrosion advancing degree of five years was achieved.

In the technique shown in Examples 1 to 12, silver sulfide with a film thickness of approximately 0.9 μm formed even in Example 1 with the thinnest film thickness. This is tantamount to the corrosion advancing degree of about two years in South Eastern Asia. That is, in the technique of Example 1, about two days are required for reproducing the corrosion advancing degree of one year. Therefore, with the use of the technique of Example 1, the acceleration test can be conducted at a speed approximately eight times as fast as that in the conventional technique shown in the Comparative Example.

What is claimed is:

1. An accelerated corrosion testing method for determining long-term reliability by means of accelerated simulation of the expected long-term corrosion in the environment of actual use for a test work piece, said accelerated corrosion testing method comprising the steps of:

providing a silver-containing test work piece to be tested for long-term corrosion characteristics;

providing a corrosion-generating gaseous mixture of clean air which additionally includes only hydrogen sulfide and nitrogen dioxide;

exposing said silver-containing test work piece to said corrosion-generating gaseous mixture to generate a film of at least one silver corrosion compound on the surface thereof and to create thereby an accelerated simulation of silver-corrosion compound generation;

identifying the presence of a test parameter of said film disposed on said test work piece and generated by exposure to said gaseous mixture;

comparing the identified test parameter of said film of said silver corrosion compound from said accelerated simulation with known standards of the same silver corrosion test parameter for silver-containing standard work pieces which have been exposed for selected periods of time to said environment of actual use; and determining from said comparison the approximate length of natural exposure time indicated thereby.

2. The corrosion testing method according to claim 1 wherein said gas mixture has a hydrogen sulfide to nitrogen dioxide concentration ratio of 1:1 to 1:3.

3. The corrosion testing method according to claim 1 wherein hydrogen sulfide and nitrogen dioxide are of concentrations of 0.7 to 2.0 ppm and 1.5 to 4.0 ppm, respectively.

4. The accelerated corrosion testing method of claim 1 wherein said exposure of said test work piece is visually monitored until a selected level of corrosion is generated, and thereafter the amount of equivalent time in exposure to the environment of actual use is determined.

5. The accelerated corrosion testing method of claim 1 wherein said generated silver corrosion compound consists essentially of silver sulfide.

6. The accelerated corrosion testing method of claim 1 wherein said generated silver corrosion compound consists essentially of silver sulfide and silver chloride.

7. The accelerated corrosion testing method of claim 1 wherein said test parameter comprises the thickness of said generated silver corrosion compound.

8. The accelerated corrosion testing method of claim 7 wherein said test parameter further includes the coarseness of grain size of said generated silver corrosion compound.

9. The accelerated corrosion testing method of claim 7 wherein said test parameter further includes the density of said generated silver corrosion compound.

10. The accelerated corrosion testing method of claim 9 wherein the visually monitored selected level of corrosion is selected based upon anticipated failure of the test work piece for its intended purpose at said selected level of corrosion.

* * * * *